(12) United States Patent
Sklar et al.

(10) Patent No.: US 8,298,285 B2
(45) Date of Patent: *Oct. 30, 2012

(54) GRAFT LIGAMENT ANCHOR AND METHOD FOR ATTACHING A GRAFT LIGAMENT TO A BONE

(75) Inventors: Joseph H. Sklar, Longmeadow, MA (US); Harold M. Martins, Newton, MA (US); Richard F. Wenstrom, Jr., Norwood, MA (US)

(73) Assignee: Joseph H. Sklar, Longmeadow, MA (US)

( * ) Notice: Subject to any disclaimer, the term of this patent is extended or adjusted under 35 U.S.C. 154(b) by 309 days.

This patent is subject to a terminal disclaimer.

(21) Appl. No.: 12/583,767

(22) Filed: Aug. 25, 2009

(65) Prior Publication Data

US 2010/0121449 A1    May 13, 2010

Related U.S. Application Data

(63) Continuation of application No. 11/184,554, filed on Jul. 19, 2005, now Pat. No. 7,578,844, which is a continuation of application No. 10/244,797, filed on Sep. 16, 2002, now Pat. No. 6,932,841, which is a continuation of application No. 09/789,398, filed on Feb. 20, 2001, now abandoned, which is a continuation of application No. 09/304,885, filed on May 4, 1999, now abandoned, which is a continuation of application No. 08/756,413, filed on Nov. 27, 1996, now Pat. No. 5,899,938.

(51) Int. Cl.
*A61F 2/08* (2006.01)
(52) U.S. Cl. ............... 623/13.14; 623/13.11; 623/13.15
(58) Field of Classification Search .................. None
See application file for complete search history.

(56) References Cited

U.S. PATENT DOCUMENTS

RE13,204 E    2/1911    Jossart
(Continued)

FOREIGN PATENT DOCUMENTS

CA    1015989    8/1977
(Continued)

OTHER PUBLICATIONS

Sklar, Joseph H., Intrafix[TM] Technique for Tibial Fixation of ACL Grafts, Innovasive Devices, a company brochure of Mitek Products, 1999.

*Primary Examiner* — David H Willse
*Assistant Examiner* — Javier Blanco
(74) *Attorney, Agent, or Firm* — Pandiscio & Pandiscio

(57) ABSTRACT

A graft ligament anchor comprises a graft ligament engagement member disposed in an opening in a bone, the graft ligament engagement member being arranged to receive a graft ligament alongside the engagement member, and a locking member for disposition in the opening, and at least in part engageable with the graft ligament engagement member. Movement of the locking member in the opening causes the locking member to urge the engagement member, and the graft ligament therewith, toward a wall of the opening, to secure the graft ligament to the wall of the opening. A method for attaching a graft ligament to a bone comprises providing an opening in the bone, inserting the graft ligament and a graft ligament engagement member in the opening, with the graft ligament disposed alongside a first portion of the engagement member, and inserting a locking member in the bone alongside a second portion of the engagement member, the locking member being separated from the graft ligament by the graft ligament engagement member. The method further comprises moving the locking member to cause the locking member to engage the graft ligament engagement member to urge the graft ligament engagement member, and the graft ligament therewith, toward a wall of the opening to secure the graft ligament to the wall of the opening.

7 Claims, 16 Drawing Sheets

U.S. PATENT DOCUMENTS

| | | |
|---|---|---|
| 2,353,851 A | 7/1944 | Rosan |
| 3,153,975 A | 10/1964 | Rapata |
| 3,199,398 A | 8/1965 | Weisz |
| 3,411,397 A | 11/1968 | Birmingham |
| 3,516,324 A | 6/1970 | Berner |
| 3,678,798 A | 7/1972 | Van Niel |
| 3,731,724 A | 5/1973 | Dorflinger |
| 3,765,295 A | 10/1973 | Ptak |
| 3,832,931 A | 9/1974 | Talan |
| 3,942,407 A | 3/1976 | Mortensen |
| 3,976,079 A | 8/1976 | Samuels et al. |
| 4,083,289 A | 4/1978 | Erickson |
| 4,085,651 A | 4/1978 | Koscik |
| 4,407,618 A | 10/1983 | Kimura |
| 4,484,570 A | 11/1984 | Sutter et al. |
| 4,535,925 A | 8/1985 | Ramey et al. |
| 4,580,936 A | 4/1986 | Francis et al. |
| 4,590,928 A | 5/1986 | Hunt et al. |
| 4,708,132 A | 11/1987 | Silvestrini |
| 4,708,397 A | 11/1987 | Weinmann |
| 4,716,893 A | 1/1988 | Fischer et al. |
| 4,744,793 A | 5/1988 | Parr et al. |
| 4,755,183 A | 7/1988 | Kenna |
| 4,778,468 A | 10/1988 | Hunt et al. |
| 4,784,126 A | 11/1988 | Hourahane |
| 4,828,562 A | 5/1989 | Kenna |
| 4,851,005 A | 7/1989 | Hunt et al. |
| 4,870,957 A | 10/1989 | Goble et al. |
| 4,927,421 A | 5/1990 | Goble et al. |
| 4,940,467 A | 7/1990 | Tronzo |
| 4,944,742 A | 7/1990 | Clemow et al. |
| 4,950,270 A | 8/1990 | Bowman et al. |
| 4,950,271 A | 8/1990 | Lewis et al. |
| 5,013,316 A | 5/1991 | Goble et al. |
| 5,037,422 A | 8/1991 | Hayhurst et al. |
| 5,062,843 A | 11/1991 | Mahony, III |
| 5,108,431 A | 4/1992 | Mansat et al. |
| 5,147,362 A | 9/1992 | Goble |
| 5,151,104 A | 9/1992 | Kenna |
| 5,152,790 A | 10/1992 | Rosenberg et al. |
| 5,211,647 A | 5/1993 | Schmieding |
| 5,234,430 A | 8/1993 | Huebner |
| 5,236,445 A | 8/1993 | Hayhurst et al. |
| 5,268,001 A | 12/1993 | Nicholson et al. |
| 5,282,802 A | 2/1994 | Mahony, III |
| 5,312,438 A | 5/1994 | Johnson |
| 5,314,427 A | 5/1994 | Goble et al. |
| 5,324,308 A | 6/1994 | Pierce |
| 5,356,435 A | 10/1994 | Thein |
| 5,360,448 A | 11/1994 | Thramann |
| 5,360,450 A | 11/1994 | Giannini |
| 5,376,119 A | 12/1994 | Zimmermann et al. |
| 5,383,878 A | 1/1995 | Roger et al. |
| 5,425,707 A | 6/1995 | Goldberg |
| 5,425,767 A | 6/1995 | Steininger et al. |
| 5,454,811 A | 10/1995 | Huebner |
| 5,458,601 A | 10/1995 | Young, Jr. et al. |
| 5,464,427 A | 11/1995 | Curtis et al. |
| 5,470,334 A | 11/1995 | Ross et al. |
| 5,480,403 A | 1/1996 | Lee et al. |
| 5,486,197 A | 1/1996 | Le et al. |
| 5,489,210 A | 2/1996 | Hanosh |
| 5,562,669 A | 10/1996 | McGuire |
| 5,584,835 A | 12/1996 | Greenfield |
| 5,618,314 A | 4/1997 | Harwin et al. |
| 5,632,748 A | 5/1997 | Beck, Jr. et al. |
| 5,645,589 A | 7/1997 | Li |
| 5,702,397 A | 12/1997 | Goble et al. |
| 5,707,395 A | 1/1998 | Li |
| 5,725,529 A | 3/1998 | Nicholson et al. |
| 5,776,196 A | 7/1998 | Matsuzaki et al. |
| 5,895,425 A | 4/1999 | Grafton et al. |
| 5,899,938 A | 5/1999 | Sklar et al. |
| 5,906,632 A | 5/1999 | Bolton |
| 5,918,604 A | 7/1999 | Whelan |
| 5,948,001 A | 9/1999 | Larsen |
| 5,961,520 A | 10/1999 | Beck, Jr. et al. |
| 5,989,253 A | 11/1999 | Bigliardi |
| 6,099,530 A | 8/2000 | Simonian et al. |
| 6,132,433 A | 10/2000 | Whelan |
| 6,283,973 B1 | 9/2001 | Hubbard et al. |
| 6,355,066 B1 | 3/2002 | Kim |
| 6,371,124 B1 | 4/2002 | Whelan |
| 6,379,361 B1 | 4/2002 | Beck, Jr. et al. |
| 6,517,579 B1 | 2/2003 | Paulos et al. |
| 6,537,319 B2 | 3/2003 | Whelan |
| 6,554,862 B2 | 4/2003 | Hays et al. |
| 6,562,071 B2 | 5/2003 | Järvinen |
| 6,575,987 B2 | 6/2003 | Gellman et al. |
| 6,616,694 B1 | 9/2003 | Hart |
| 6,623,524 B2 | 9/2003 | Schmieding |
| 6,632,245 B2 | 10/2003 | Kim |
| 6,673,094 B1 | 1/2004 | McDevitt et al. |
| 6,733,529 B2 | 5/2004 | Whelan |
| 6,746,483 B1 | 6/2004 | Bojarski et al. |
| 6,887,271 B2 | 5/2005 | Justin et al. |
| 6,939,379 B2 | 9/2005 | Sklar |
| 7,008,451 B2 | 3/2006 | Justin et al. |
| 7,261,716 B2 | 8/2007 | Strobel et al. |
| 7,309,355 B2 | 12/2007 | Donnelly et al. |
| 7,329,281 B2 | 2/2008 | Hays et al. |
| 2001/0007074 A1 | 7/2001 | Strobel et al. |
| 2001/0047206 A1 | 11/2001 | Sklar et al. |
| 2002/0007182 A1 | 1/2002 | Kim |
| 2002/0040241 A1 | 4/2002 | Jarvinen |
| 2002/0072797 A1 | 6/2002 | Hays et al. |
| 2003/0065390 A1 | 4/2003 | Justin et al. |
| 2003/0135274 A1 | 7/2003 | Hays et al. |
| 2003/0144735 A1 | 7/2003 | Sklar et al. |
| 2003/0191530 A1 | 10/2003 | Sklar |
| 2004/0059415 A1 | 3/2004 | Schmieding |
| 2004/0068262 A1 | 4/2004 | Lemos et al. |
| 2004/0194789 A1 | 10/2004 | Whelan |
| 2004/0267361 A1 | 12/2004 | Donnelly et al. |
| 2005/0159748 A1 | 7/2005 | Clark |
| 2005/0171603 A1 | 8/2005 | Justin et al. |
| 2005/0216012 A1 | 9/2005 | Willmen |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0149258 A1 | 7/2006 | Sousa |
| 2006/0189991 A1 | 8/2006 | Bickley |
| 2007/0005069 A1 | 1/2007 | Contiliano et al. |
| 2008/0015710 A1 | 1/2008 | Hays et al. |
| 2008/0133007 A1 | 6/2008 | Donnelly et al. |
| 2008/0154314 A1 | 6/2008 | McDevitt |
| 2008/0161806 A1 | 7/2008 | Donnelly et al. |
| 2008/0161864 A1 | 7/2008 | Beck et al. |
| 2008/0228271 A1 | 9/2008 | Stone et al. |

FOREIGN PATENT DOCUMENTS

| | | |
|---|---|---|
| CA | 2272960 | 6/1998 |
| DE | 1015989 | 9/1957 |
| DE | 8901338.7 | 3/1989 |
| DE | 8914308.6 | 3/1990 |
| DE | 9109381.3 | 9/1991 |
| DE | 4127550 | 2/1993 |
| EP | 0358372 | 3/1990 |
| EP | 0425140 | 5/1991 |
| EP | 0596177 | 5/1994 |
| EP | 0596829 | 5/1994 |
| EP | 0651979 | 5/1995 |
| EP | 0834281 | 4/1998 |
| EP | 1491162 | 12/2004 |
| FR | 2590792 | 6/1987 |
| FR | 2636835 | 3/1990 |
| JP | 05-300917 | 11/1993 |
| JP | 6-169944 | 6/1994 |
| JP | 8-66410 | 3/1996 |
| WO | WO 94/28799 | 12/1994 |
| WO | WO 98/22047 | 5/1998 |
| WO | WO 98/23229 | 6/1998 |
| WO | WO 99/52472 | 10/1999 |
| WO | WO 01/06909 | 2/2001 |
| WO | WO 01/30253 | 5/2001 |
| WO | WO 01/95835 | 12/2001 |
| WO | WO 02/32345 | 4/2002 |

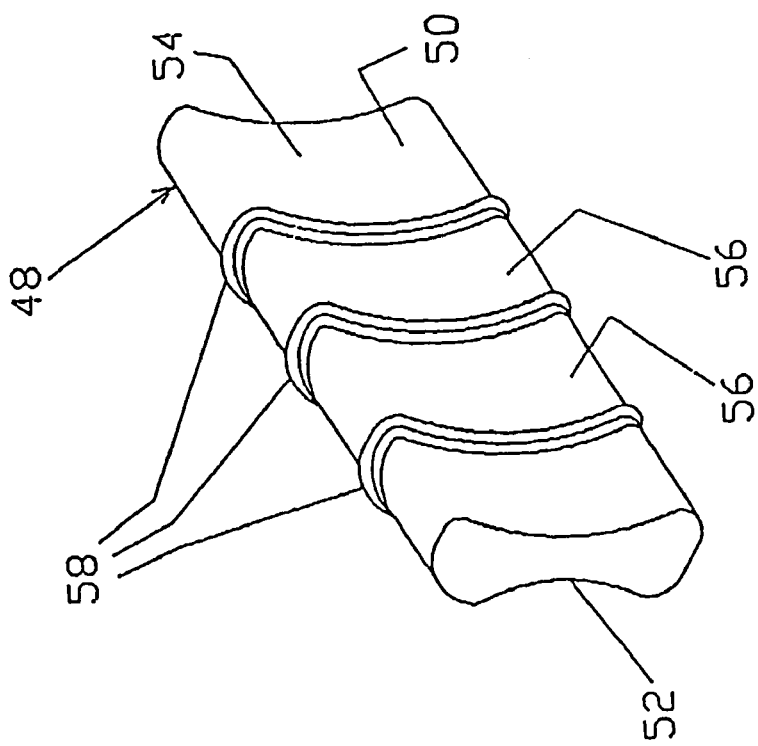
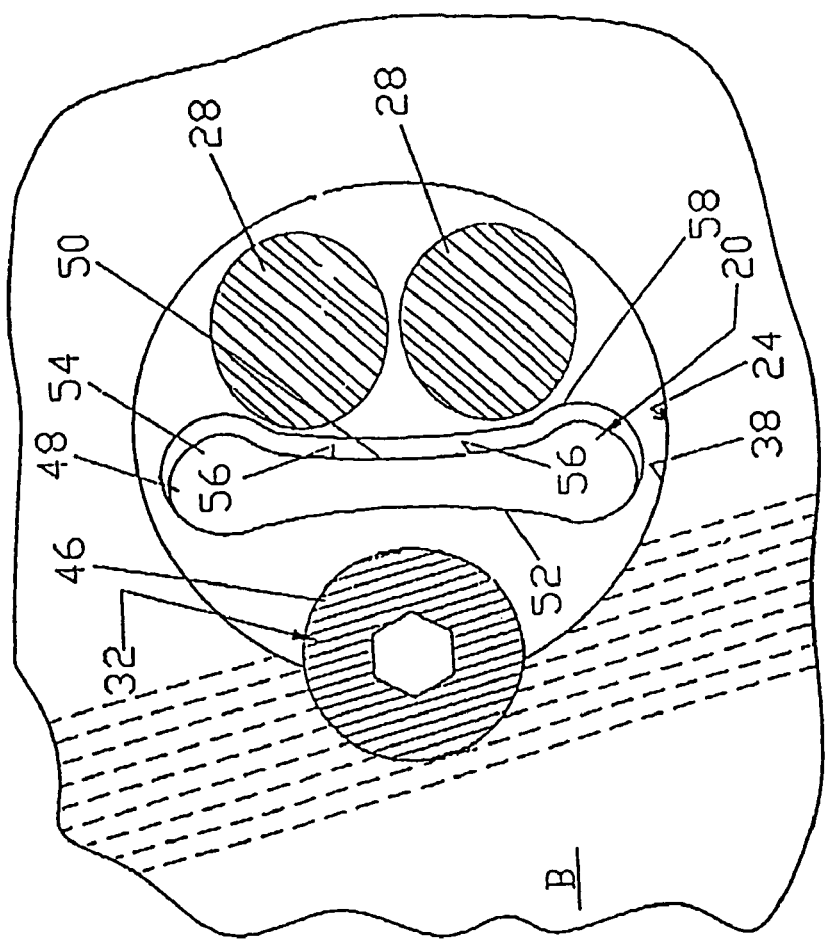

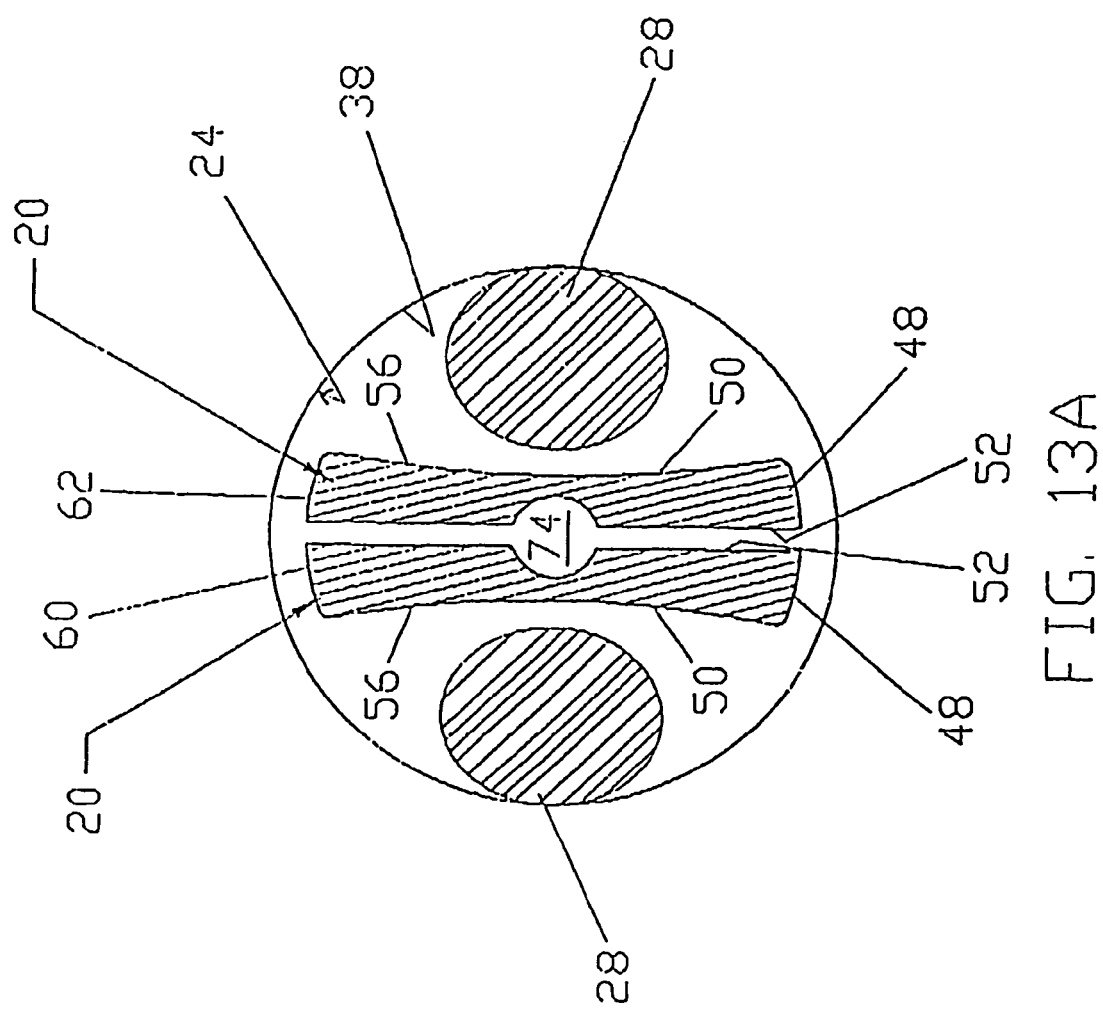

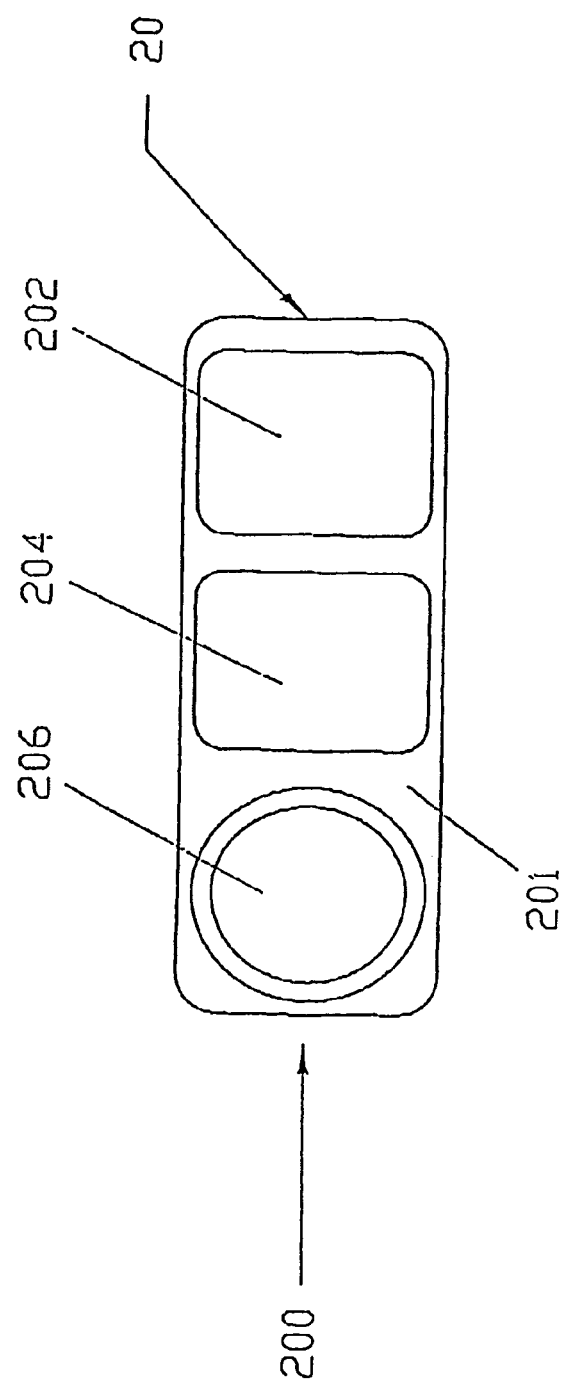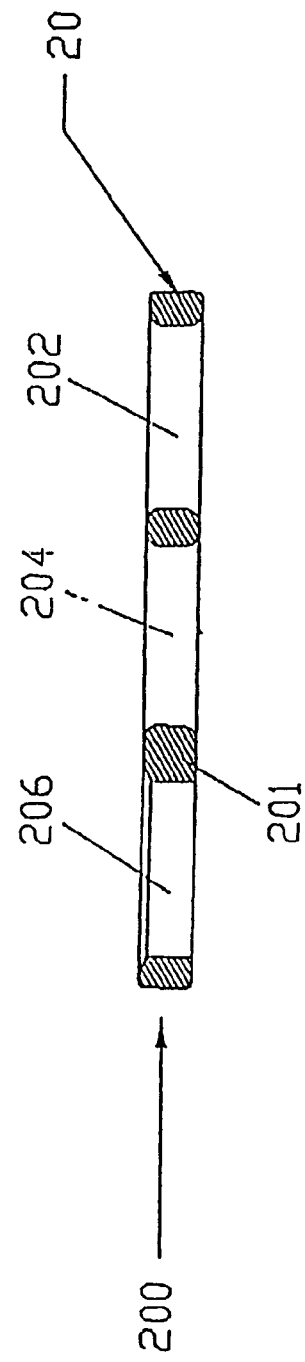

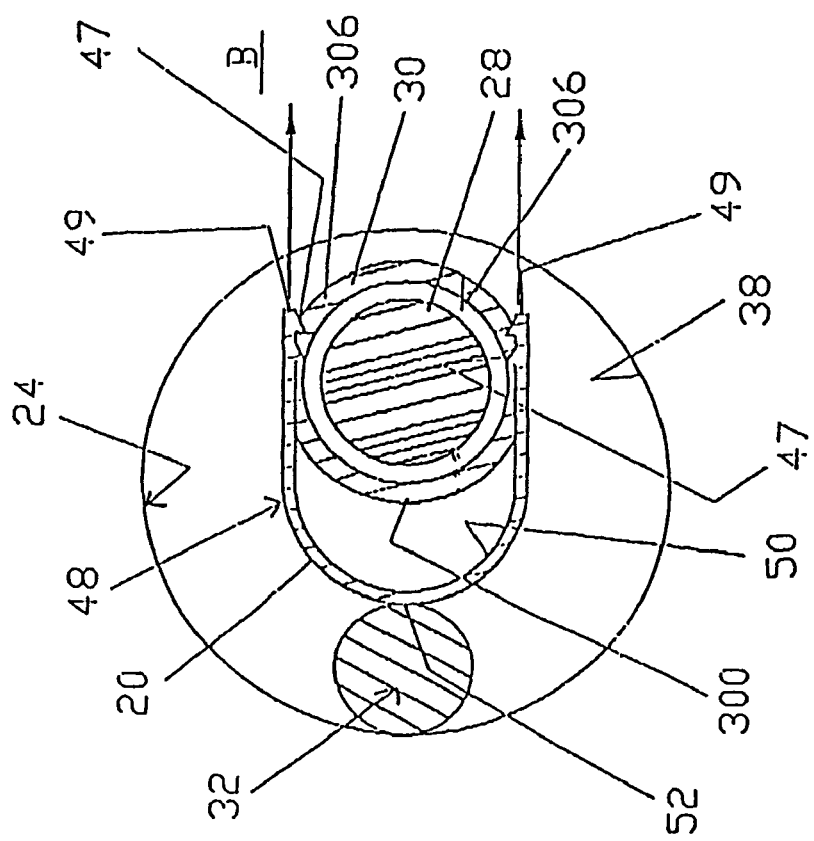
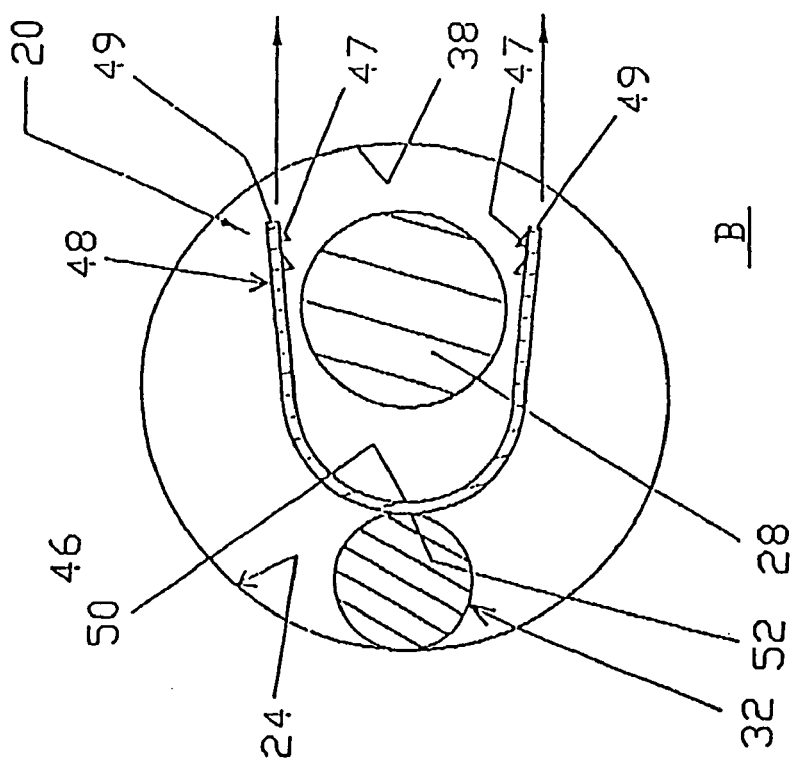
FIG. 22
FIG. 20

GRAFT LIGAMENT ANCHOR AND METHOD FOR ATTACHING A GRAFT LIGAMENT TO A BONE

REFERENCE TO PENDING PRIOR PATENT APPLICATIONS

This patent application is a continuation of prior U.S. patent application Ser. No. 11/184,554, filed Jul. 19, 2005 now U.S. Pat. No. 7,578,844 by Joseph H. Sklar et al. for GRAFT LIGAMENT ANCHOR AND METHOD FOR ATTACHING A GRAFT LIGAMENT TO A BONE, which in turn is a continuation of prior U.S. patent application Ser. No. 10/244,797, filed Sep. 16, 2002 now U.S. Pat. No. 6,932,841 by Joseph H. Sklar et al. for GRAFT LIGAMENT ANCHOR AND METHOD FOR ATTACHING A GRAFT LIGAMENT TO A BONE, which in turn is a continuation of prior U.S. patent application Ser. No. 09/789,398, filed Feb. 20, 2001 now abandoned by Joseph H. Sklar et al. for GRAFT LIGAMENT ANCHOR AND METHOD FOR ATTACHING A GRAFT LIGAMENT TO A BONE, which in turn is a continuation of prior U.S. patent application Ser. No. 09/304,885, filed May 4, 1999 now abandoned by Joseph H. Sklar et al. for GRAFT LIGAMENT ANCHOR AND METHOD FOR ATTACHING A GRAFT LIGAMENT TO A BONE, which in turn is a continuation of prior U.S. patent application Ser. No. 08/756,413, filed Nov. 27, 1996 now U.S. Pat. No. 5,899,938 by Joseph H. Sklar et al. for GRAFT LIGAMENT ANCHOR AND METHOD FOR ATTACHING A GRAFT LIGAMENT TO A BONE.

The five above-identified patent applications are hereby incorporated herein by reference.

FIELD OF THE INVENTION

This invention relates to medical apparatus and methods in general, and more particularly to apparatus and methods for reconstructing ligaments.

BACKGROUND OF THE INVENTION

Ligaments are tough bands of tissue which serve to connect the articular extremities of bones, or to support or retain organs in place within the body. Ligaments are typically composed of coarse bundles of dense white fibrous tissue which are disposed in a parallel or closely interlaced manner, with the fibrous tissue being pliant and flexible, but not significantly extensible.

In many cases, ligaments are torn or ruptured as a result of accidents. As a result, various procedures have been developed to repair or replace such damaged ligaments.

For example, in the human knee, the anterior and posterior cruciate ligaments (i.e., the ACL and PCL) extend between the top end of the tibia and the bottom end of the femur. The ACL and PCL cooperate, together with other ligaments and soft tissue, to provide both static and dynamic stability to the knee. Often, the anterior cruciate ligament (i.e., the ACL) is ruptured or torn as a result of, for example, a sports-related injury. Consequently, various surgical procedures have been developed for reconstructing the ACL so as to restore normal function to the knee.

In many instances, the ACL may be reconstructed by replacing the ruptured ACL with a graft ligament. More particularly, with such procedures, bone tunnels are typically formed in the top end of the tibia and the bottom end of the femur, with one end of the graft ligament being positioned in the femoral tunnel and the other end of the graft ligament being positioned in the tibial tunnel. The two ends of the graft ligament are anchored in place in various ways known in the art so that the graft ligament extends between the femur and the tibia in substantially the same way, and with substantially the same function, as the original ACL. This graft ligament then cooperates with the surrounding anatomical structures so as to restore normal function to the knee.

In some circumstances the graft ligament may be a ligament or tendon which is harvested from elsewhere in the patient; in other circumstances the graft ligament may be a synthetic device. For the purposes of the present invention, all of the foregoing can be collectively referred to as a "graft ligament".

As noted above, the graft ligament may be anchored in place in various ways. See, for example, U.S. Pat. No. 4,828,562, issued May 9, 1989 to Robert V. Kenna; U.S. Pat. No. 4,744,793, issued May 17, 1988 to Jack E. Parr et al.; U.S. Pat. No. 4,755,183, issued Jul. 5, 1988 to Robert V. Kenna; U.S. Pat. No. 4,927,421, issued May 22, 1990 to E. Marlowe Goble et al.; U.S. Pat. No. 4,950,270, issued Aug. 21, 1990 to Jerald A. Bowman et al.; U.S. Pat. No. 5,062,843, issued Nov. 5, 1991 to Thomas H. Mahony, III; U.S. Pat. No. 5,147,362, issued Sep. 15, 1992 to E. Marlowe Goble; U.S. Pat. No. 5,211,647, issued May 18, 1993 to Reinhold Schmieding; U.S. Pat. No. 5,151,104, issued Sep. 29, 1992 to Robert V. Kenna; U.S. Pat. No. 4,784,126, issued Nov. 15, 1988 to Donald H. Hourahane; U.S. Pat. No. 4,590,928, issued May 27, 1986 to Michael S. Hunt et al.; and French Patent Publication No. 2,590,792, filed Dec. 4, 1985 by Francis Henri Breard.

Despite the above-identified advances in the art, there remains a need for a graft ligament anchor which is simple, easy to install, and inexpensive to manufacture, while providing secure, trouble-free anchoring of the graft ligament, typically in the knee joint of a mammal.

OBJECTS OF THE INVENTION

Accordingly, one object of the present invention is to provide an improved graft ligament anchor which is relatively simple in construction and therefore inexpensive to manufacture, relatively easy to handle and install, and reliable and safe in operation.

Another object of the present invention is to provide an improved method for attaching a graft ligament to a bone.

SUMMARY OF THE INVENTION

These and other objects of the present invention are addressed by the provision and use of a novel graft ligament anchor comprising graft ligament engagement means for disposition in an opening in a bone, such that a wall of the graft ligament engagement means resides adjacent to at least one graft ligament disposed in the opening, and locking means for disposition in the opening in the bone and at least partially engageable with the graft ligament engagement means. The elements of the graft ligament anchor are adapted such that movement of the locking means in the opening in the bone causes at least a part of the locking means to engage the graft ligament engagement means so as to urge the graft ligament engagement means, and hence the portion of the graft ligament disposed adjacent thereto, toward a wall of the opening in the bone, whereby to secure the graft ligament to the wall of the opening.

In use, an opening is made in the bone, and the graft ligament and the graft ligament engagement means are inserted into the opening, with a portion of the graft ligament being disposed alongside a wall of the graft ligament engagement means. In accordance with the present invention, the locking means are also positioned in the opening in the bone, alongside the graft ligament engagement means, with the locking means being separated from the graft ligament by a portion of the graft ligament engagement means. The method further includes moving the locking means in the opening in the bone so as to cause at least a portion thereof to urge the graft ligament engagement means, and hence the portion of the graft ligament disposed adjacent thereto, toward a wall of the opening, whereby to secure the graft ligament to the wall of the opening.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 8 is a diagrammatic sectional view of yet another form of graft ligament anchor made in accordance with the present invention;

FIG. 9 is a perspective view of one of the components of the graft ligament anchor shown in FIG. 8;

FIG. 13A is a diagrammatic sectional view of still another form of ligament anchor made in accordance with the present invention;

FIG. 14 is a top plan view of still another form of graft ligament anchor made in accordance with the present invention;

FIG. 15 is a side view, in section, of the graft ligament anchor shown in FIG. 14;

FIG. 20 is a diagrammatic sectional view of still another form of graft ligament anchor made in accordance with the present invention;

FIG. 22 is a diagrammatic sectional view of still another form of graft ligament anchor made in accordance with the present invention.

DETAILED DESCRIPTION OF THE PREFERRED EMBODIMENTS

Figure 1:
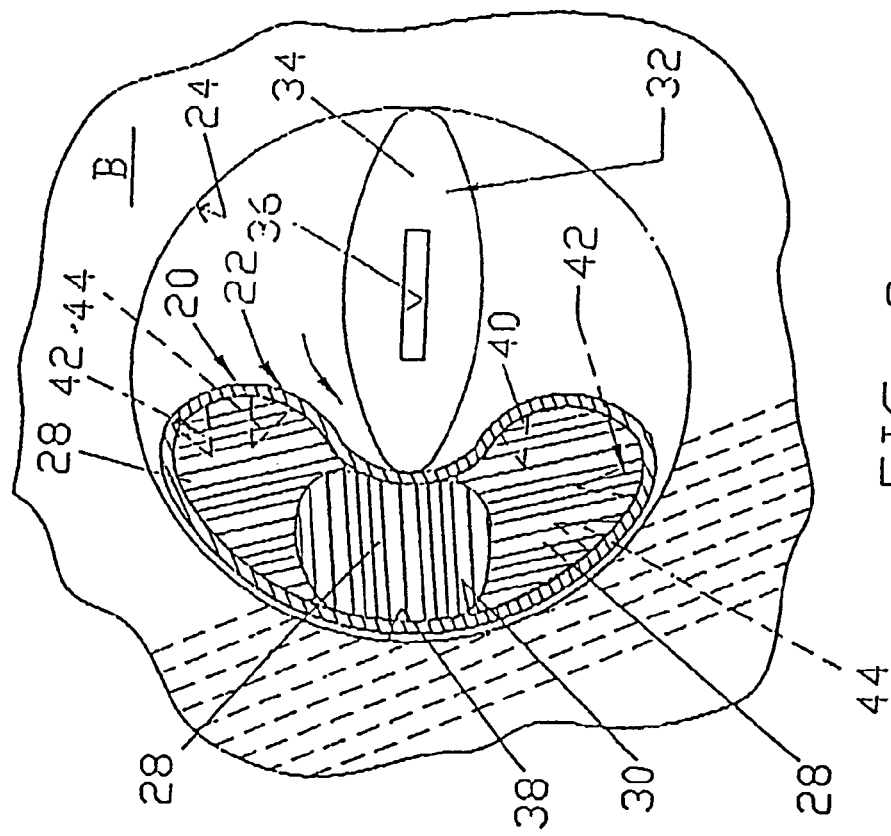
FIG. 1 is a diagrammatic sectional view of one form of graft ligament anchor made in accordance with the present invention.

Referring first to FIG. 1, it will be seen that one illustrative embodiment of the present invention includes a graft ligament engagement means 20 comprising a deformable sleeve 22, preferably formed out of metal or plastic, and adapted to be inserted into an opening 24 formed in a bone B. One or more graft ligaments 28 are disposed alongside an interior wall 30 of sleeve 22.

The embodiment illustrated in FIG. 1 further includes locking means 32, which may be a pivotally movable rocker arm 34, which may be provided with a slot 36 for receiving a key member (not shown) for turning rocker arm 34.

Figure 2:
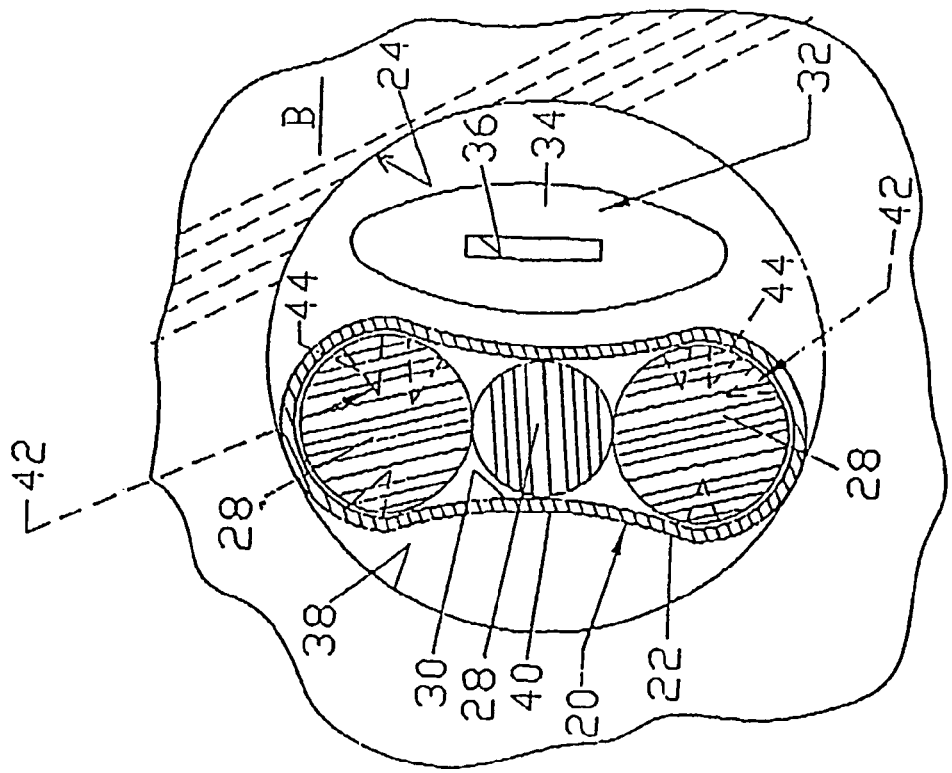
FIG. 2 is similar to FIG. 1, but shows the graft ligament anchor components in different operating positions.

Referring to FIG. 2, it will be seen that turning rocker arm 34 enables a portion of the rocker arm to impinge upon an exterior surface 40 of sleeve 22 so as to force sleeve 22, and hence graft ligaments 28 contained therein, toward sidewall 38 of opening 24, whereby to secure sleeve 22 and graft ligaments 28 between opening sidewall 38 and locking means 32.

In operation, opening 24 is first made in bone B and then graft ligaments 28 and graft ligament engagement means 20 are inserted into opening 24, with graft ligaments 28 being disposed alongside a first wall, i.e., the interior wall 30, of sleeve 22. Locking means 32 are inserted into opening 24 alongside the exterior surface 40 of sleeve 22. Locking means 32 are thus separated from graft ligaments 28 by graft ligament engagement means 20, i.e., sleeve 22. As noted above, movement of locking means 32 causes at least a portion thereof to engage sleeve 22 and to crimp the sleeve inwardly upon graft ligaments 28, and to push both sleeve 22 and graft ligaments 28 against sidewall 38 of opening 24.

If it is desired to thereafter release graft ligaments 28, rocker arm 34 may be moved back to the position shown in FIG. 1. To this end, graft ligament engagement means 20 preferably are formed out of a resilient material, whereby engagement means 20 can return to substantially the same position shown in FIG. 1 when locking means 32 return to the position shown in FIG. 1.

If desired, substantially all of sleeve 22 can be formed so as to be deformable; alternatively, some of sleeve 22 can be formed so as to be rigid. By way of example, the portion of sleeve 22 contacted by locking means 32 can be formed so as to be substantially rigid.

Graft ligaments 28 may comprise natural or synthetic graft ligament material, and the anchor can be used to attach natural or synthetic graft ligaments and/or tendons to bone. Sleeve 22 preferably is provided with inwardly-extending protrusions 42, such as spikes 44, for securely retaining graft ligaments 28 therein.

Figure 3:
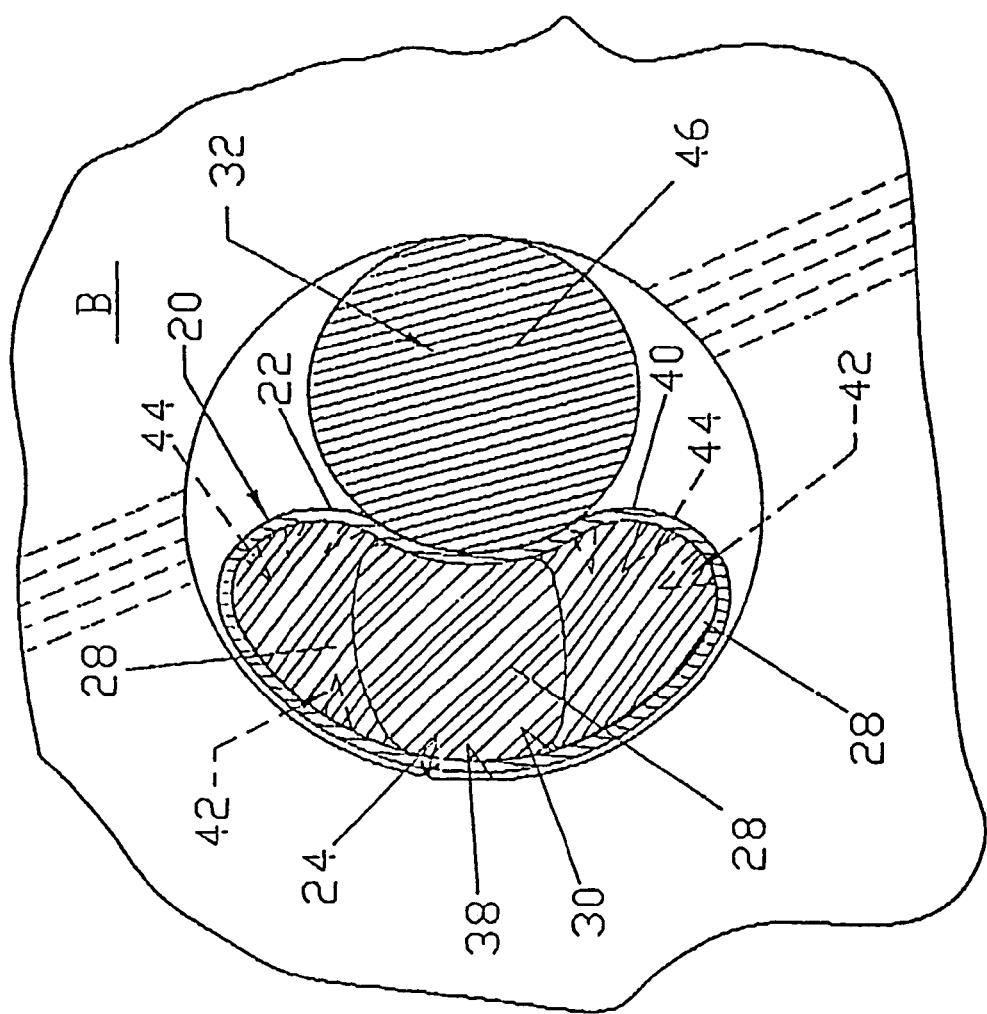
FIG. 3 is similar to FIG. 1, but shows an alternative embodiment of the present invention.

Locking means 32 may be a rocker arm type, such as the rocker arm member 34 shown in FIGS. 1 and 2, or a generally conically-shaped expansion plug 46, as shown in FIG. 3, with the expansion plug preferably being threaded such that as the plug is screwed into place, an increasing diameter of the plug engages sleeve 22 in a wedge-like manner so as to force the sleeve against interior wall 38 of opening 24.

Figure 4:
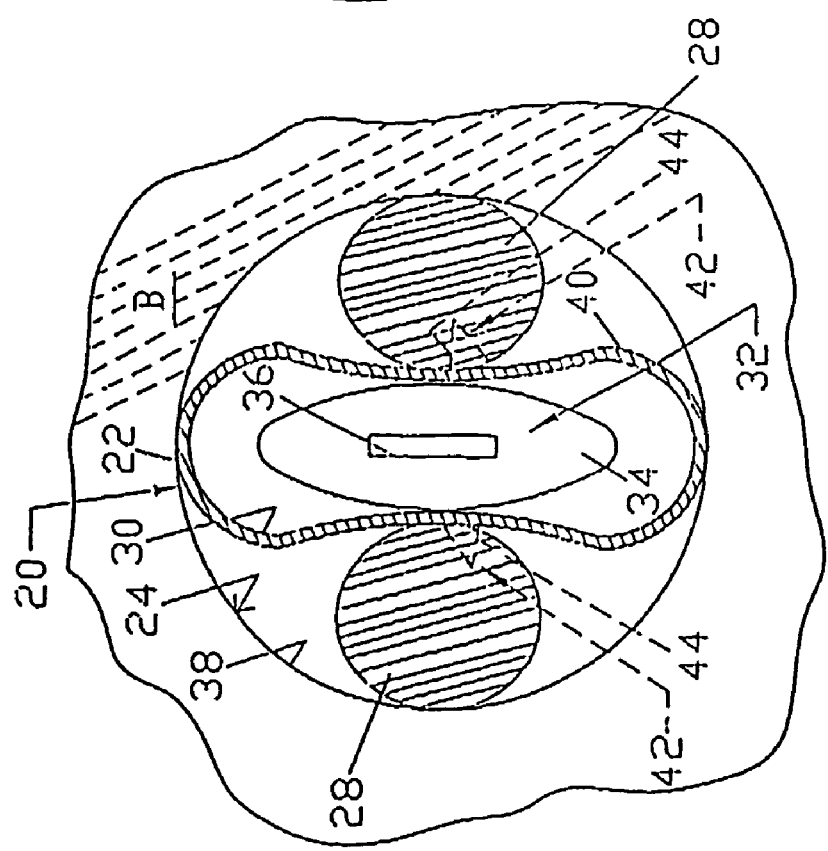
FIG. 4 is a diagrammatic sectional view of another form of graft ligament anchor made in accordance with the present invention.

In FIG. 4, there is shown an alternative embodiment in which graft ligaments 28 are disposed alongside exterior wall 40 of sleeve 22, and locking means 32 is disposed within sleeve 22. With this embodiment, locking means 32 operate to engage interior wall 30 of the sleeve (FIG. 5), whereby to force graft ligaments 28 against sidewall 38 of opening 24. Again, locking means 32 may be a rocker arm type, such as the rocker arm member 34 shown in FIGS. 4 and 5, or may be an expansion plug 46, preferably threaded, of the sort shown in FIG. 3. With the embodiment shown in FIGS. 4 and 5, sleeve 22 may be provided with protrusions 42 (in the form of spikes 44, for example) on the exterior wall 40 thereof for engagement with graft ligaments 28. In many instances, it is beneficial to provide at least two discrete graft ligaments 28 and, in such cases, it is preferable that the graft ligaments be disposed on substantially opposite diametric sides of the sleeve, as shown in FIGS. 4 and 5.

Figure 5:
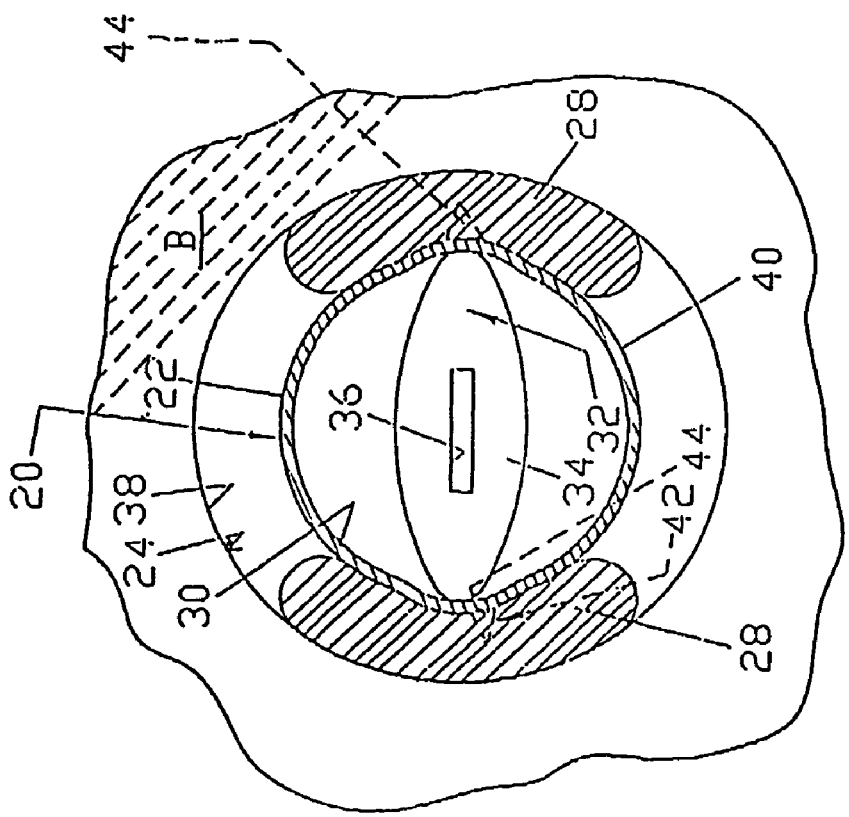
FIG. 5 is similar to FIG. 4, but shows the graft ligament anchor components in different operating positions.
Figure 6:
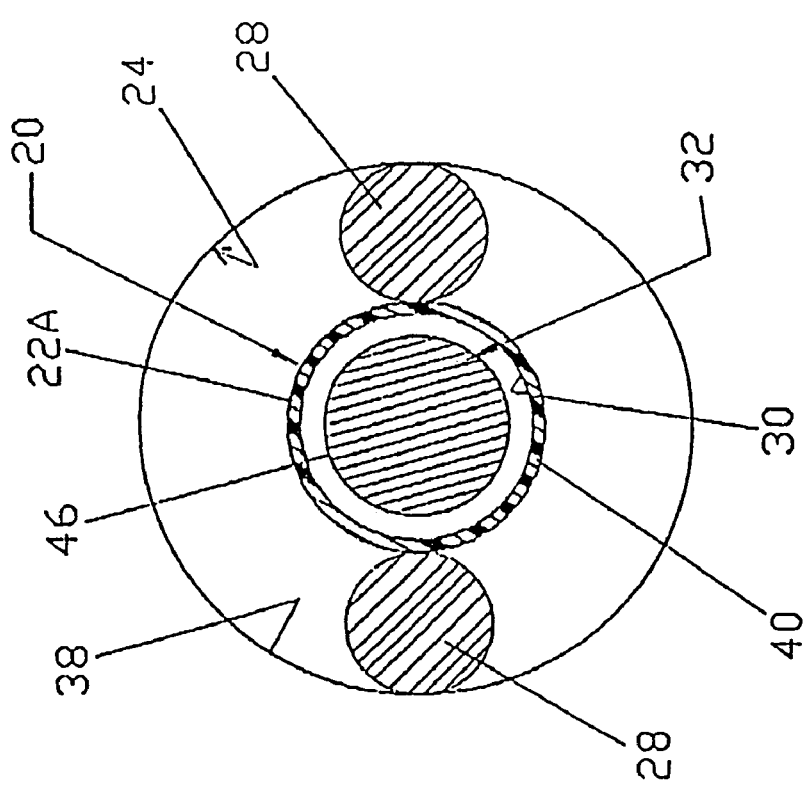
FIG. 6 is a diagrammatic sectional view of another form of graft ligament anchor made in accordance with the present invention.

In FIG. 6, there is shown an embodiment similar to that shown in FIGS. 4 and 5, but provided with an expandable sleeve 22A, rather than a deformable metal or plastic sleeve 22 as shown in FIGS. 1-5. Sleeve 22A may be formed out of an elastomeric material, and it is expanded radially outwardly by engagement with a centrally disposed locking means 32 (preferably in the form of a threaded expansion plug 46) so as to force graft ligaments 28 outward into a secured position between sleeve 22A and opening sidewall 38.

In operation, the embodiments shown in FIGS. 4-6 function similarly to the embodiments shown in FIGS. 1-3 in attaching graft ligaments 28 to bone B. Opening 24 is first made in bone B. Graft ligaments 28 and graft ligament engagement means 20 (in the form of sleeve 22 or sleeve 22A) are inserted into opening 24, with graft ligaments 28 disposed alongside exterior wall 40 of the graft ligament engagement means, i.e., alongside the exterior wall 40 of sleeve 22 or sleeve 22A. Locking means 32 (in the form of a rocker arm member 34 or a threaded expansion plug 46) are inserted axially into the sleeve, alongside interior wall 30 of the sleeve. Locking means 32 are thus separated from the graft ligaments 28 by the sleeve (22 or 22A). Then locking means 32 are manipulated so as to engage the sleeve (22 or 22A) and thereby urge the sleeve, and hence graft ligaments 28, toward opening sidewall 38, whereby to secure the sleeve and graft ligaments to the wall of the opening.

If and when it is desired to adjust tension on graft ligaments 28, locking means 32 may be backed off, that is, if locking means 32 comprise the rocker arm type cam member 34, the arm need only be rotated 90° from the positions shown in FIGS. 2 and 5, to return to the positions shown, respectively, in FIGS. 1 and 4; if, on the other hand, locking means 32 comprise expansion plug 46, the plug need only be unscrewed or otherwise axially withdrawn so as to release the securing of the graft ligaments.

Figure 7:
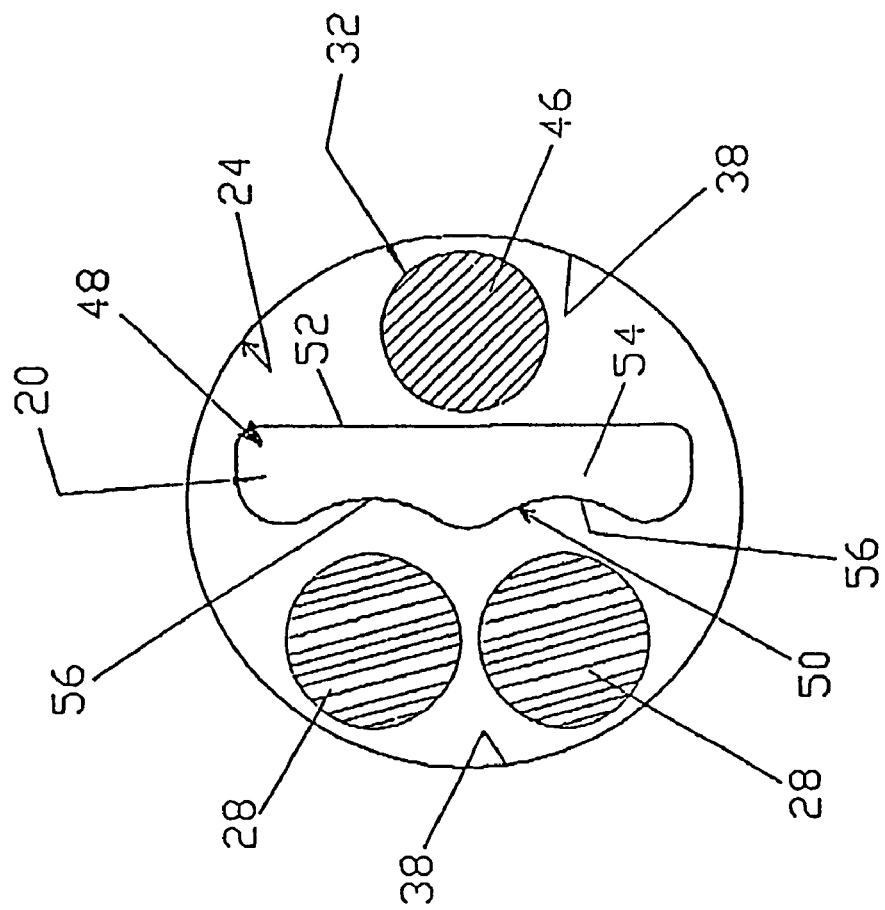
FIG. 7 is a diagrammatic sectional view of still another form of graft ligament anchor made in accordance with the present invention.

Referring next to FIG. 7, it will be seen that in an alternative embodiment, graft ligament engagement means 20 comprises plate means 48 which are movable transversely within the bone opening. As in the embodiments previously described, graft ligaments 28 are disposed alongside a wall 50 of graft ligament engagement means 20, which in this instance is a first major surface of plate means 48. Graft ligament engagement means 20 are disposed between graft ligaments 28 and locking means 32. Locking means 32 may be, as in the above-described embodiments, an expansion plug 46 (as shown in FIG. 7), or locking means 32 may be a rocker arm type of cam member 34 (of the sort shown in FIGS. 1, 2, 4 and 5). Locking means 32 are adapted to impinge upon a second major surface 52 of plate means 48. Plate means 48, in the embodiment shown in FIG. 7, comprises a single plate 54 having, on first major surface 50 thereof, one or more concavities 56 for nesting one or more graft ligaments 28, respectively.

In the attachment of one or more graft ligaments 28 to a bone B, using the embodiment of FIG. 7, locking means 32 are manipulated so as to bear against plate 54 so as to move plate 54 into engagement with graft ligaments 28, and thence to further move plate 54 so as to secure the graft ligaments against sidewall 38 of opening 24.

Referring next to FIG. 8, it will be seen that locking means 32 may comprise the threaded expansion plug 46 deployed partly in opening 24 and threaded partly into bone B, thus serving as a so-called interference screw. With this arrangement, plug 46 is thereby (i) in part along its length disposed in opening 24, protruding into the opening from opening wall 38, and (ii) in part along its length threadedly engaged with bone B. Screwing in plug 46 causes the plug to engage plate 54 which, in turn, compacts one or more graft ligaments 28 against wall 38 of opening 24.

In lieu of, or in addition to, the aforementioned concavities 56 shown in FIG. 7, plate 54 may be provided with gripper ribs 58 for engaging graft ligaments 28, as shown in FIGS. 8 and 9.

Figure 10:
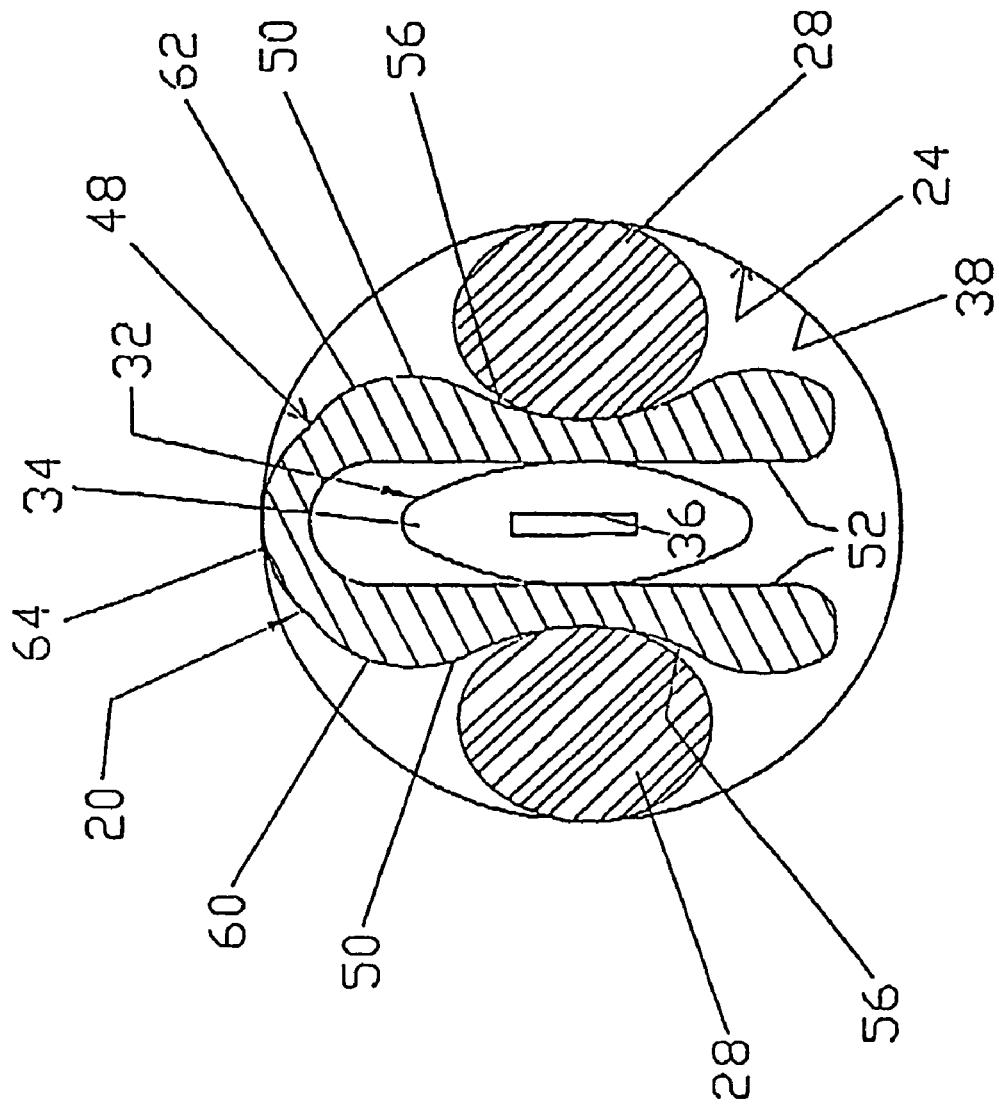
FIG. 10 is a diagrammatic sectional view of still another form of graft ligament anchor made in accordance with the present invention.

In FIG. 10, it is shown that plate means 48 may include first and second plates 60, 62, each having a wall 50 facing one or more graft ligaments 28, and a wall 52 facing locking means 32. Plates 60, 62 may be joined together by a link 64 which may be molded integrally with plates 60, 62 so as to form a so-called "living hinge" link. Locking means 32 are depicted in FIG. 10 as a rocker arm type of cam member 34, but it will be appreciated that an expansion plug type of locking means (e.g., a plug 46 such as that shown in FIGS. 3, 6 and 7) might also be used.

In operation, rotative movement of rocker arm 34 (or axial movement of expansion plug 46) causes plates 60, 62 to move outwardly from each other so as to urge graft ligaments 28 against wall 38 of opening 24. Walls 50 of plates 60, 62 may be provided with concavities 56, as shown in FIG. 10, or with ribs 58 of the sort shown in FIG. 9, or both.

Figure 11:
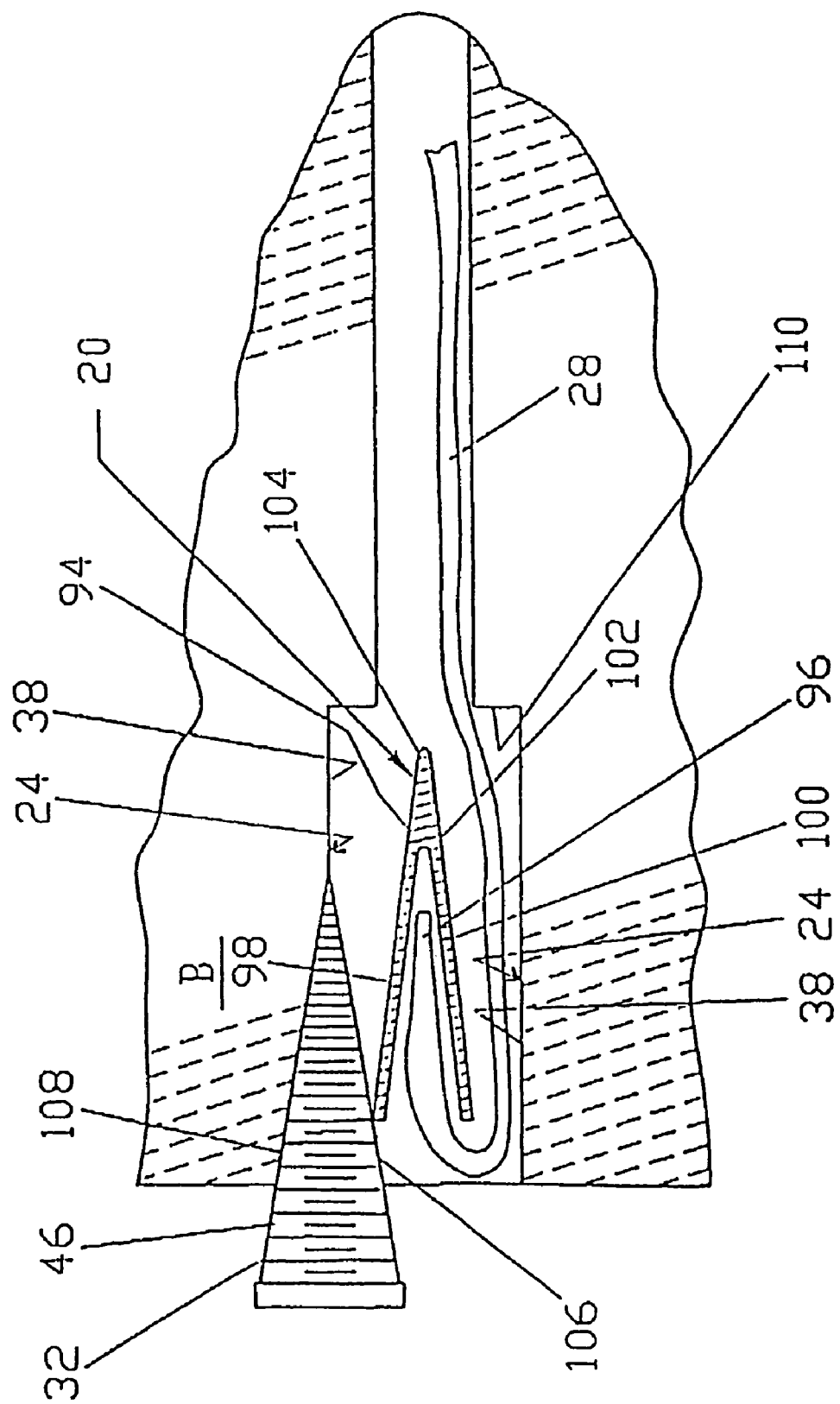
FIG. 11 is a diagrammatic view of still another form of graft ligament anchor made in accordance with the present invention.

Referring next to FIG. 11, it will be seen that still another embodiment of the present invention includes, as graft ligament engagement means 20, a V-shaped strip 94, preferably made out of a resilient metal or plastic material. An end portion 96 of a graft ligament 28 is disposed between first and second leg portions 98, 100 of V-shaped strip 94, and graft ligament 28 extends alongside an exterior surface 102 of second leg portion 100. Locking means 32 comprise a threaded expansion plug 46 disposed partly in opening 24 and partly in bone B, along sidewall 38 of opening 24, in a manner similar to the disposition of threaded expansion plug 46 shown in FIG. 8.

Upon screwing in expansion plug 46, the expansion plug engages first leg 98 of graft ligament engagement means 20 (i.e., the V-shaped strip 94) to force first leg 98 to close upon second leg 100 with the graft ligament end portion 96 sandwiched therebetween and, upon further screwing in of threaded expansion plug 46, to force graft ligament engagement means 20 and graft ligament 28 against wall 38 of opening 24. To release graft ligament 28, an operator need only back out expansion plug 46.

When attaching a graft ligament to a bone with the graft ligament anchor shown in FIG. 11, an opening is first drilled, or otherwise made, in the bone. Then the V-shaped strip 94 is inserted into the opening, with a nose portion 104 thereof pointed inwardly of the bone. Next, end portion 96 of graft ligament 28 is inserted between first and second leg portions 98, 100 of V-shaped strip 94. Threaded expansion plug 46 is then inserted into opening wall 38 such that a first portion 106 of the lengthwise extent of plug 46 is disposed in opening 24, and second portion 108 of the lengthwise extent of plug 46 is threadedly engaged with bone B. Expansion plug 46 is then screwed further down so as to cause plug 46 to engage first leg 98 of V-shaped strip 94 so as to secure graft ligament end portion 96 in V-shaped strip 94, and then screwed down further to wedge strip 94 and graft ligament 28 against wall 38 of opening 24.

Still referring to FIG. 11, it is to be appreciated that bone opening 24 may be formed with a constant diameter throughout its length or, if desired, may be formed with two different diameters along its length, in the manner shown in FIG. 11, so as to form an annular shoulder 110 within the bone opening. The provision of an annular shoulder 110 can be very helpful in ensuring that the graft ligament anchor is prevented from migrating further into bone B, even if graft ligament 28 should thereafter be subjected to substantial retraction forces.

In a modification (not shown) of the FIG. 11 embodiment, the expansion plug 46 may be entered alongside graft ligament 28 and second leg portion 100 of strip 94. In this modified version, the expansion plug 46 operates as described above, except that expansion plug 46 engages graft ligament 28 and forces strip first leg 98 against wall 38 of opening 24.

Figure 13:
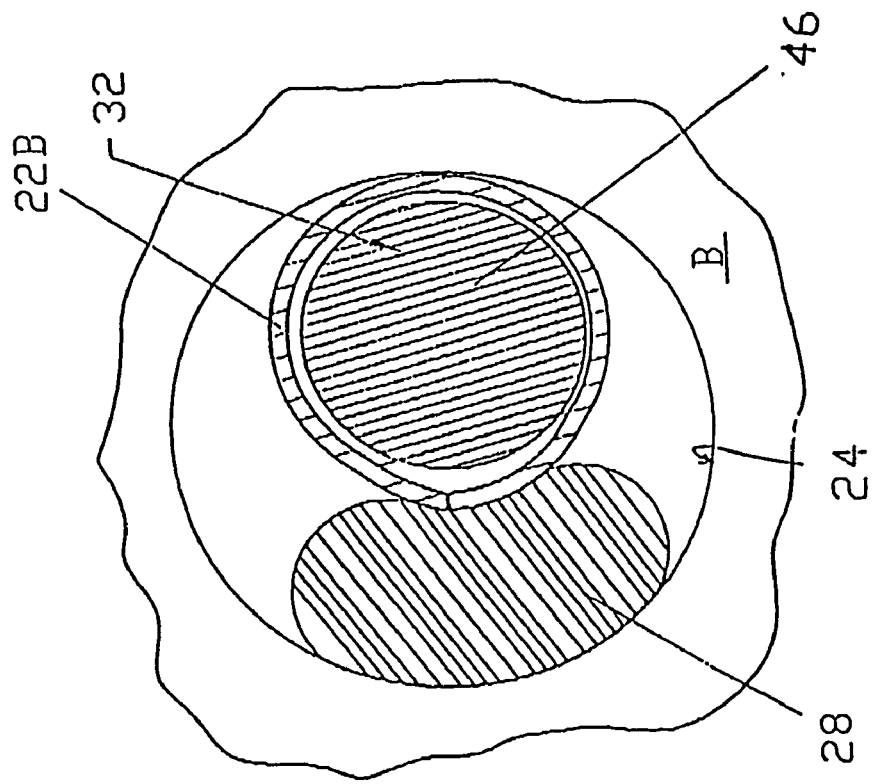
FIG. 13 is similar to FIG. 12, but shows the graft ligament anchor components in different operating conditions.
Figure 12:
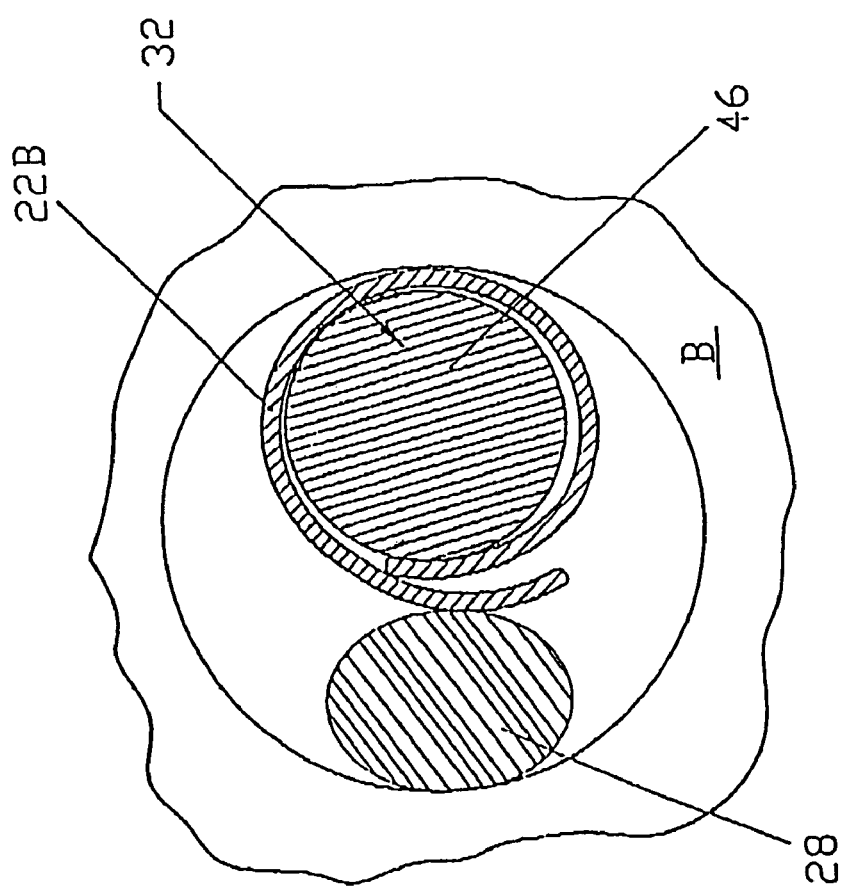
FIG. 12 is a diagrammatic sectional view of yet another form of graft ligament anchor made in accordance with the present invention.

Looking next at FIGS. 12 and 13, yet another form of graft ligament anchor is disclosed. This graft ligament anchor is similar to the embodiment shown in FIG. 6, except that the expandable sleeve 22B is in the form of a cylindrical coil. Sleeve 22B is formed out of an elastomeric material and is expanded radially outwardly by engagement with a centrally disposed locking means 32 (preferably an axially-movable threaded expansion plug 46) so as to force graft ligament 28 outward into a secured position between sleeve 22B and bone B.

In FIG. 13A there is shown an embodiment similar to that shown in FIG. 10, but in which the first and second plates 60, 62 are discrete plates and not connected to each other. With this arrangement, locking means 32 is inserted into a central recess 74 defined by plate walls 52, and may comprise either an expansion plug 46 of the type shown in FIGS. 6 and 7 or a rocker arm type of cam member 34 of the type shown in FIGS. 1 and 2.

Looking next at FIGS. 14 and 15, another graft ligament anchor 200 is shown. Anchor 200 includes graft ligament engagement means 20 comprising a flat plate 201, a pair of through-holes 202, 204 and a threaded through-hole 206. In use, and looking now at FIGS. 14, 15 and 16, the free end 96 of graft ligament 28 is passed downward through hole 202 and then back upward again through hole 204, and then a screw 208 is used to secure anchor 200 to the wall 210 of the bone opening by threading the shank of screw 208 through hole 206, through graft ligament 28, and into bone B. This will cause screw 208 and plate 201 to securely attach graft ligament 28 to bone B.

Figure 16:
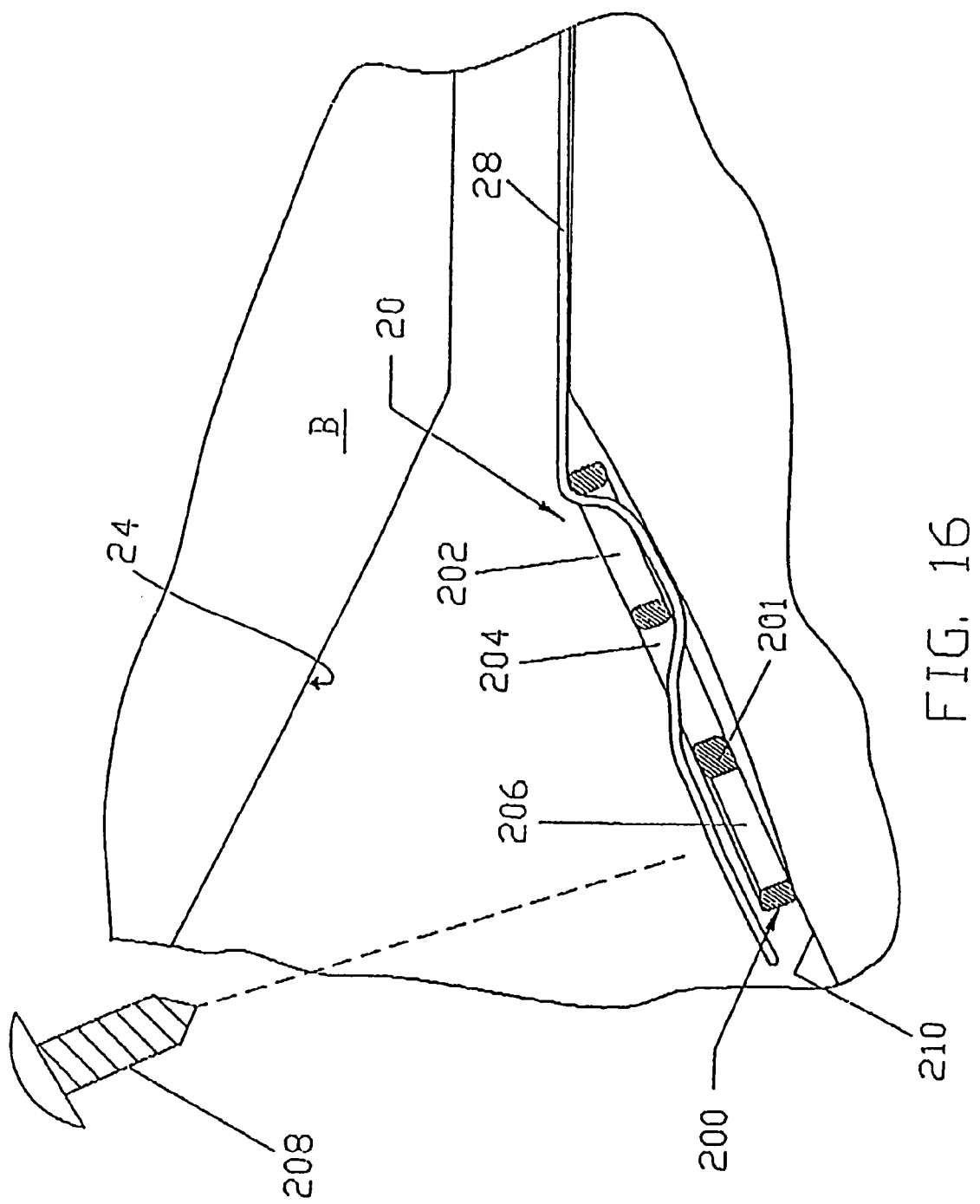
FIG. 16 is a side view showing the graft ligament anchor of FIGS. 14 and 15 securing a graft ligament to a bone.
Figure 17:
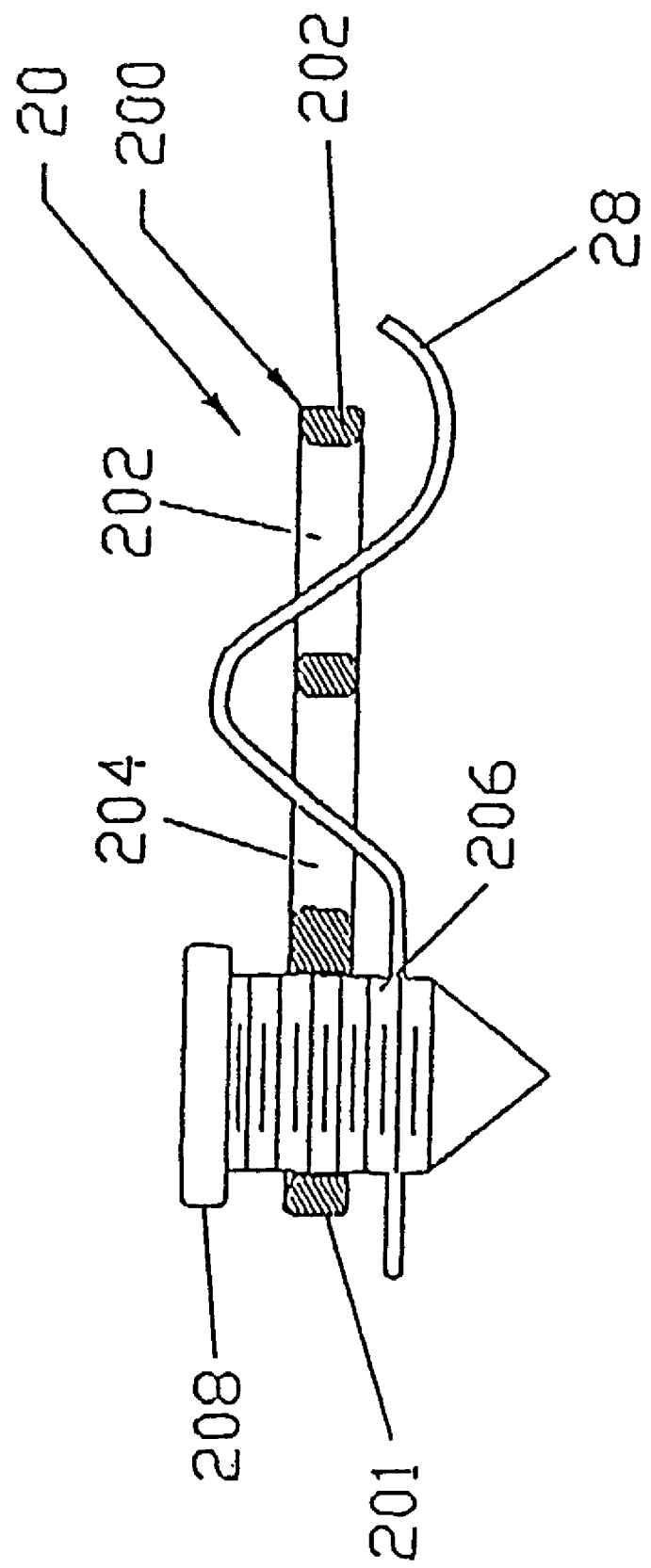
FIG. 17 is similar to a portion of FIG. 16, but showing components of the graft ligament anchor and graft ligament of FIG. 16 in alternative positions.

As shown in FIG. 17, alternatively, graft ligament 28 may be passed upwardly through hole 202 and downwardly through hole 204. Screw 208 is then threaded through hole 206 and graft ligament 28 and into bone B. Thus, as in the embodiment shown in FIG. 16, screw 208 and plate 201 secure graft ligament 28 to bone B.

Figure 18:
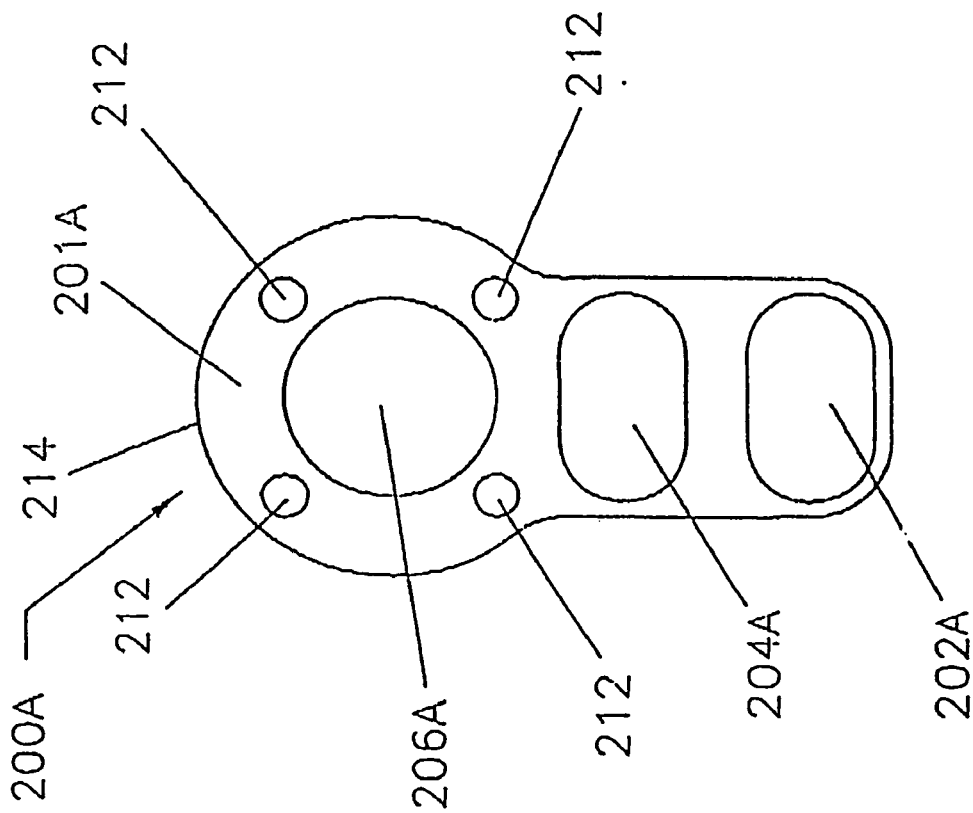
FIG. 18 is a top plan view of yet another form of graft ligament anchor made in accordance with the present invention.
Figure 19:
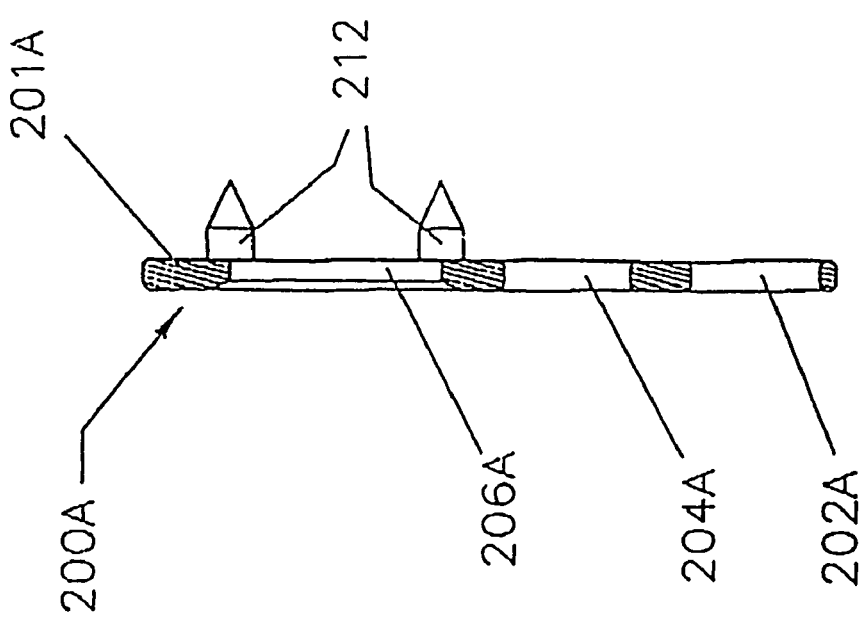
FIG. 19 is a side view, in section, of the graft ligament anchor shown in FIG. 18.

FIGS. 18 and 19 show another graft ligament anchor 200A. Graft ligament anchor 200A is similar to graft ligament anchor 200, except that it includes a plurality of spikes 212 for projecting into wall 210 (FIG. 16) of bone B when the graft ligament anchor is deployed against the bone. Also, graft ligament anchor 200A has an enlarged configuration 214 in the region of through-hole 206A, as shown in FIG. 18.

Figure 21:
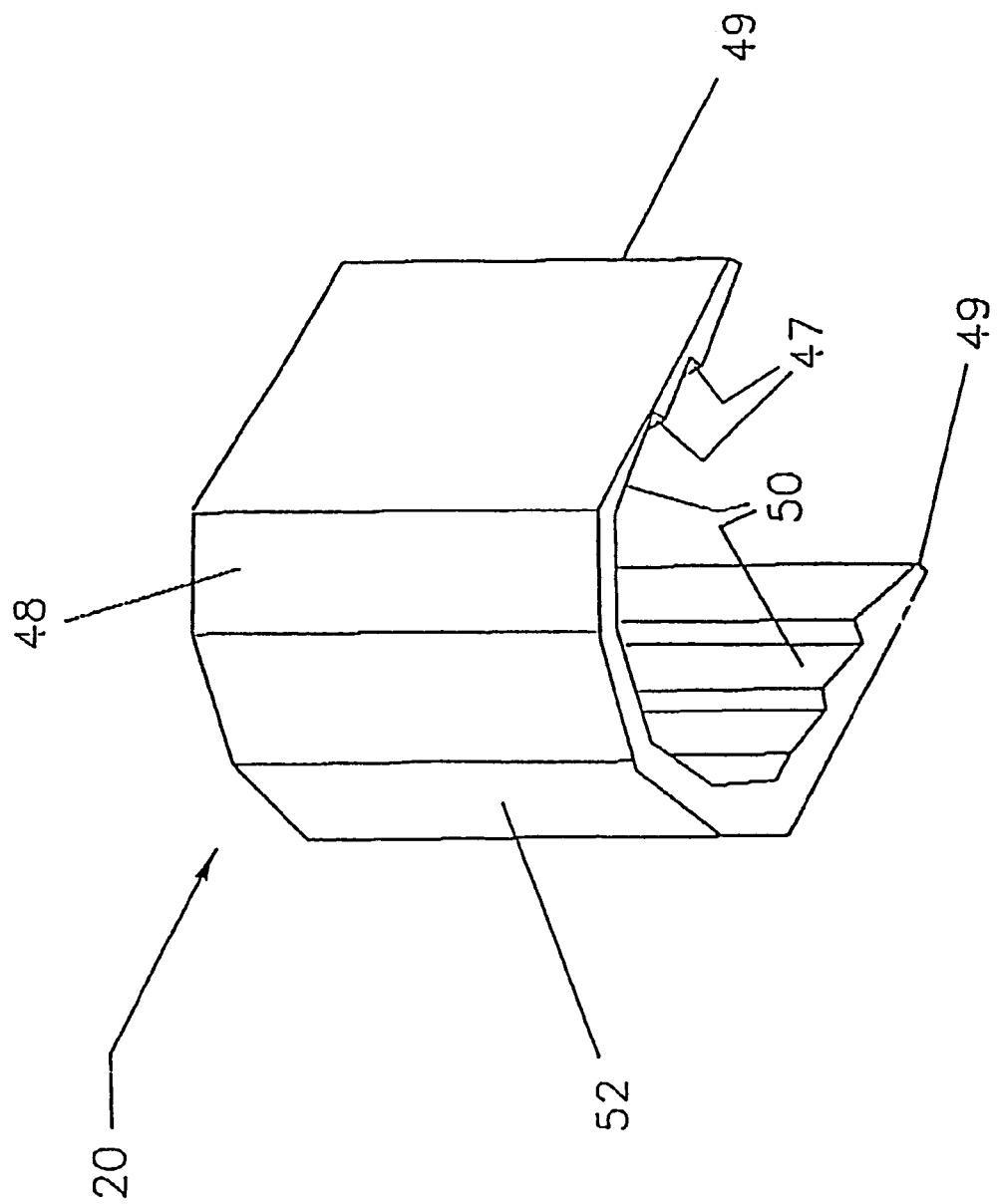
FIG. 21 is a perspective view of a component of the graft ligament anchor shown in FIG. 20.

Referring next to FIG. 20, there is shown a still further alternative embodiment of graft ligament anchor, similar to that shown in FIG. 7, wherein graft ligament engagement means 20 comprises plate means 48 formed in a U-shaped configuration (FIG. 21) movable transversely within bone opening 24. At least one graft ligament 28 is disposed alongside wall 50 of graft ligament engagement means 20, which in this instance is a first major surface of plate means 48. Graft ligament engagement means 20 is disposed between graft ligament 28 and locking means 32. Locking means 32 may be an expansion plug 46, as shown in FIG. 20 and in FIG. 7, or a rocker arm type cam member 34, as shown in FIG. 1, or an interference screw type expansion plug 46, as shown in FIG. 11, or a transverse screw 208, as shown in FIG. 16.

In attachment of one or more graft ligaments 28 to a bone B, using the embodiment of FIG. 20, locking means 32 is manipulated so as to bear against a second major surface 52 of plate means 48 and thereby move plate means 48 into engagement with graft ligament 28, and thence to drive free ends 49 of plate means 48 into sidewall 38 of opening 24 so as to fasten graft ligament 28 to sidewall 38 and, thereby, to bone B.

Figure 23:
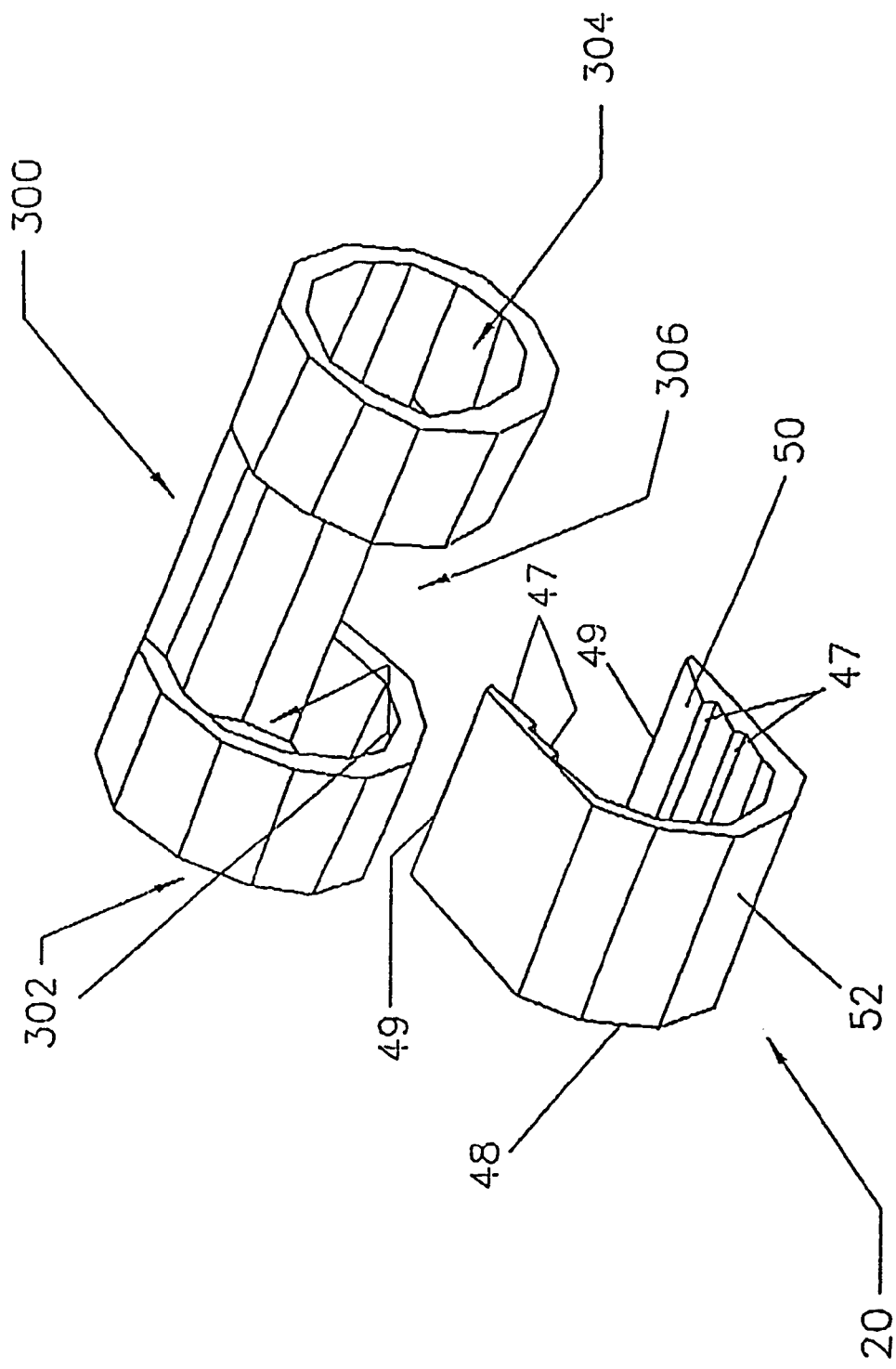
FIG. 23 is a perspective view of components of the graft ligament anchor of FIG. 22.

Referring to FIGS. 22 and 23, there is shown still another alternative embodiment of graft ligament anchor including a tubular member 300, open at first and second ends 302, 304 and having an opening 306 in the sidewall thereof. Otherwise, the graft ligament anchor of FIG. 22 is similar to the graft ligament anchor of FIG. 20, described hereinabove.

In attachment of one or more graft ligaments 28 to a bone, using the embodiment of FIGS. 22 and 23, locking means 32 are manipulated to bear against second major surface 52 of plate means 48 so as to move plate means 48 through tubular member opening 306 and into engagement with graft ligament 28, and thence further to drive free ends 49 of plate means 48 into sidewall 38 of opening 24, whereby to fasten tubular member 300 and graft ligament 28 to sidewall 38 and, thereby, to bone B. In this embodiment, and in the embodiments shown in FIGS. 1-3, an operator may fasten the graft ligament to the bone without the graft ligament contacting the bone. The tubular member 300 preferably is of a plastic or metallic material and the plate means 48 is of a plastic or metallic material. In the embodiments shown in FIGS. 20 and 22, the plate means 48 may be provided with interior teeth 47 for gripping graft ligament 28.

It is to be understood that the present invention is by no means limited to the particular constructions and methods herein disclosed and/or shown in the drawings, but also comprises any modifications or equivalents within the scope of the claims.

What is claimed is:
1. A method for attaching a graft ligament to a bone, the method comprising the steps of:
   providing an opening in the bone;
   inserting the graft ligament and a deformable tubular sleeve in the opening, with the graft ligament disposed alongside an inner wall of the deformable sleeve;

inserting a rocker arm type cam member in the opening proximate an outer wall of the sleeve, the rocker arm type cam member being separated from the graft ligament by the sleeve; and pivotally moving the rocker arm type cam member to cause at least a portion thereof to engage the sleeve to urge the sleeve, and hence the graft ligament, toward and into tight engagement with a wall of the opening to secure the graft ligament to the wall of the opening, wherein said inner wall of said sleeve is provided with inwardly extending protrusions for engaging said graft ligament.

2. A graft ligament anchor assembly comprising:

a deformable tubular sleeve adapted for insertion into an opening formed in a bone;

a graft ligament disposed alongside an inner wall of said sleeve; and a pivotally moveable rocker arm type cam member for insertion in said bone opening proximate an inner wall of said sleeve, said rocker arm type cam member being rotatably movable in said bone opening to impinge upon the outer wall of said sleeve to force said sleeve and hence said graft ligament therein toward and into tight engagement with a sidewall of the bone opening;

whereby to secure said sleeve and said graft ligament therein between said rocker arm type cam member and the sidewall of the opening in the bone, wherein said inner wall of said sleeve is provided with inwardly extending protrusions for engaging said graft ligament.

3. A graft ligament anchor assembly according to claim 2 wherein said sleeve is adapted to accommodate a discrete second graft ligament disposed alongside an inner wall of said sleeve.

4. A graft ligament anchor assembly according to claim 3 wherein said sleeve is adapted to accommodate said graft ligaments on substantially opposite diametric sides of said sleeve.

5. A graft ligament anchor assembly according to claim 2 wherein said sleeve is of metal.

6. A graft ligament anchor assembly according to claim 2 wherein said sleeve is adapted to accommodate a discrete second graft ligament disposed alongside said inner wall of said sleeve, said rocker arm type cam member being operable to urge said sleeve, with said graft ligaments therein, against said sidewall of said bone opening.

7. The graft ligament anchor assembly in accordance with claim 2 wherein said rocker arm type cam member is provided with a slot adapted to receive a key member for turning said rocker arm type cam member.

* * * * *